United States Patent [19]

Imai et al.

[11] Patent Number: 5,055,415

[45] Date of Patent: Oct. 8, 1991

[54] METHOD FOR IMMUNOASSAY PROCEDURE FOR THE DETECTION OF ANTIGEN BY REACTING WITH ANTIBODY WHICH INCREASES ITS ELECTRICAL CHARGE AND ELECTROPHORETIC MOBILITY

[75] Inventors: Kyoko Imai, Katsuta; Yasushi Nomura, Mito, both of Japan

[73] Assignee: Hitachi, Ltd., Tokyo, Japan

[21] Appl. No.: 177,347

[22] Filed: Apr. 1, 1988

[30] Foreign Application Priority Data

Apr. 1, 1987 [JP] Japan .................................. 62-80038

[51] Int. Cl.$^5$ .......................................... G01N 33/561
[52] U.S. Cl. .................................. 436/516; 204/182.3; 436/518; 436/530; 436/531; 436/535; 436/536; 436/538; 436/806; 436/819
[58] Field of Search ............... 436/516, 518, 530, 531, 436/535, 806, 815, 817, 819, 538, 536; 204/182.3

[56] References Cited

U.S. PATENT DOCUMENTS

| | | | |
|---|---|---|---|
| 3,654,090 | 4/1972 | Schuurs et al. | 436/817 |
| 3,966,897 | 6/1976 | Renn et al. | 436/516 |
| 4,048,298 | 9/1977 | Niswender | 436/535 |
| 4,287,300 | 9/1981 | Gibbons et al. | 436/806 |
| 4,628,035 | 12/1986 | Tokinaga et al. | 436/516 |

OTHER PUBLICATIONS

B. R. Clark et al., in E.T. Maggio (ed.), *Enzyme-Immunoassay*, CRC Press, Inc., Boca Raton, Fla., 1980, pp. 167–179.

*Primary Examiner*—David A. Saunders
*Attorney, Agent, or Firm*—Antonelli, Terry, Stout & Kraus

[57] ABSTRACT

A method for immunoassay for an antigen involves the following steps: reacting a sample possibly containing an antigen to be determined, a definite amount of a conjugate of the antigen and a charged substance and a definite amount of labeled antibody specific for antigen; allowing the reaction products to electrophoretically migrate towards a carrier bearing an attached antibody specific for the charged substance, so that when the reaction products contact the carrier any reaction product of labeled antibody and antigen passes through the carrier and any reaction product of the labeled antibody and conjugate binds to the carrier attached antibody specific for the charged substance; determining the amount of labeled antibody thereby bound to the carrier and relating the determined amount of labeled antibody to the amount of antigen in the sample.

8 Claims, 4 Drawing Sheets

F I G. 2
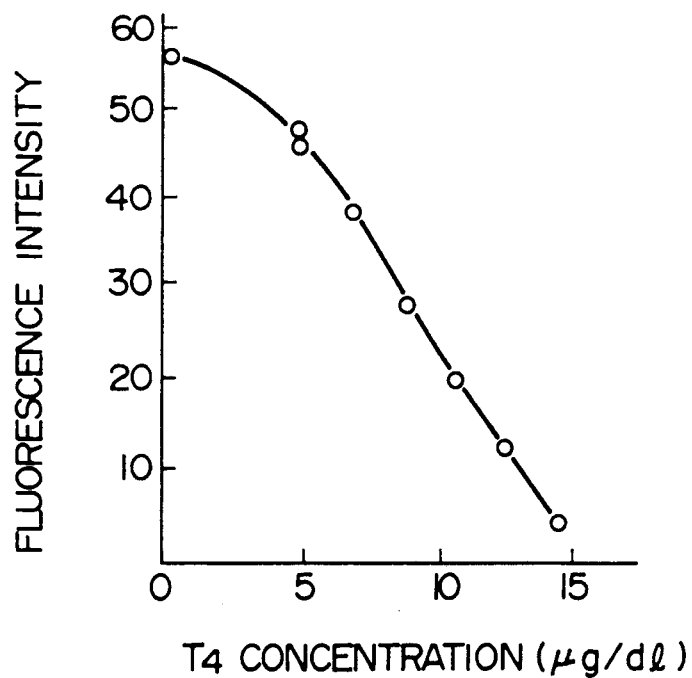
F I G. 3
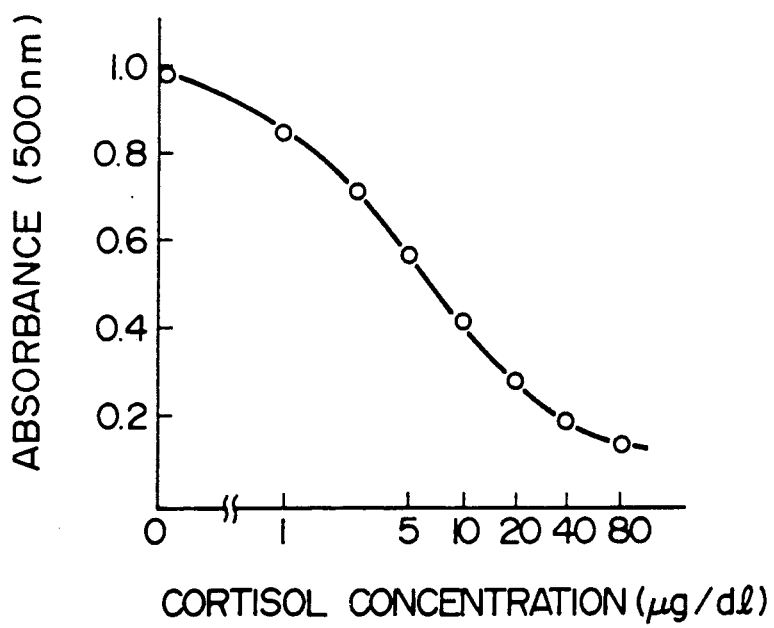

METHOD FOR IMMUNOASSAY PROCEDURE FOR THE DETECTION OF ANTIGEN BY REACTING WITH ANTIBODY WHICH INCREASES ITS ELECTRICAL CHARGE AND ELECTROPHORETIC MOBILITY

BACKGROUND OF THE INVENTION

1. Field of the Invention

This invention relates to a method for immunoassay, particularly to a method for immunoassay in which an antigenic substance which is apparently electrically neutral or has no or slight electric charge is electrified to be enabled to migrate by electrophoresis, or in which an antigenic substance which has an electric charge is more electrified to be improved in migration property, whereby the substance is advantageously quantitated.

2. Related Art Statement

A typical example of immunoassay which have been made practicable heretofore is radioimmunoassay. However, radioimmunoassay requires troublesome operations. Therefore, a highly sensitive immunoassay utilizing electrophoresis was developed. A method related to this immunoassay is disclosed, for example, in U.S. Pat. No. 4,628,035. In this immunoassay using electrophoresis, a reaction carrier is provided between an anode and a cathode in electrophoretic apparatus, and an antibody reactive specifically with a substance to be determined has been previously attached to the reaction carrier. The substance to be determined is allowed to arrive at the reaction carrier by electrophoretic migration and subjected to antigen-antibody reaction with the antibody reactive specifically with the substance to be determined in the carrier. According to this method, upon quantitating a substance to be determined in a sample, contaminating materials in the sample which cause measurement errors are merely passed through the reaction carrier by electrophoresis and prevented from being held therein, and hence they do not affect the antigen-antibody reaction in the reaction carrier. Therefore, according to this method, the good precision of measurement can be achieved, and even trace constituents of blood can be determined with high sensitivity because the substance to be determined is concentrated in the reaction carrier by electrophoresis.

However, for analyzing a substance to be determined by the above method the arrival of the substance to be determined at the reaction carrier by electrophoretic migration is an essential. When the substance to be determined is one which has an electric charge such as a protein component, the immunoassay utilizing electrophoresis can be effectively practised. However, electrophoresis is not applicable to a substance to be determined which has no electric charge. Therefore, the above method is disadvantageous, for examples, in that quantitation of a substance which is apparently electrically neutral or has no or slight electric charge is not taken into consideration, so that quantitation of a hapten such a steroidal hormone is difficult. Furthermore, the above method is disadvantageous in that where a substance to be determined which has originally an electric charge exists in a sample at very low concentration, the substance becomes not to have a high migration property and therefore the substance can not be determined with high sensitivity.

SUMMARY OF THE INVENTION

Accordingly, an object of the present invention is to provide a method for immunoassay by which an antigen to be determined which is apparently electrically neutral or has no or slight electric charge is quantitated with high precision and with high sensitivity by utilizing electrophoresis.

Another object of the present invention is to provide a method in which antigen to be determined which has an electric charge is more electrified to be improved in migration property, whereby the antigen is quantitated with high sensitivity and with high precision.

Further, another object of the present invention is to provide a kit for the above methods.

The method for immunoassay of the present invention comprises reacting an antigen to be determined with a definite amount of an antibody reactive specifically with the antigen to electrify the antigen or to more electrify the antigen; allowing the reaction products to migrate by electrophoresis toward a reaction carrier provided between an anode and a cathode in an electrophoretic apparatus; holding directly or indirectly the antibody which has not reacted with the antigen to be determined or the antibody which has reacted with the antigen to be determined, on the reaction carrier; determining directly or indirectly the amount of the unreacted antibody or the reacted antibody by label measurement; and thereby quantitating the antigen to be determined in a sample.

For determining an antigen to be determined, by the method for immunoassay of this invention, the following four methods are preferable.

A first method for immunoassay comprises reacting the antigen to be determined with a definite amount of a labeled antibody reactive specifically with the antigen to be determined; previously attaching, on the other hand, the same antigen as the antigen to be determined to the reaction carrier; allowing the reaction products to migrate toward the reaction carrier by electrophoresis; passing the reaction product of the antigen to be determined and the labeled antibody reacted therewith, through the reaction carrier; binding the unreacted labeled antibody to the same antigen as the antigen to be determined attached to the reaction carrier, to hold the unreacted labeled antibody on the reaction carrier; determining the amount of the unreacted labeled antibody by label measurement; and thereby quantitating the antigen to be determined in the sample.

A second method for immunoassay comprises reacting the antigen to be determined and a definite amount of a combined product of the same antigen as the antigen to be determined and a charged substance with a definite amount of a labeled antibody reactive specifically with the antigen to be determined; previously attaching, on the other hand, an antibody reactive specifically with the charged substance to the reaction carrier; allowing the reaction products to migrate toward the reaction carrier by electrophoresis; passing the reaction product of the antigen to be determined and the labeled antibody reacted therewith, through the reaction carrier; binding the labeled antibody reacted with the combined product of the same antigen as the antigen to be determined and the charged substance as well as the unreacted combined product, to the antibody reactive specifically with the charged substance which has been attached to the reaction carrier, to hold the labeled antibody on the reaction carrier; determining the amount of the labeled antibody held on the reaction carrier by label measurement; and thereby quantitating the antigen to be determined in the sample.

A third method for immunoassay comprises reacting the antigen to be determined and a definite amount of a combined product of the same antigen as the antigen to be determined and a labeled charged substance with a definite amount of a first antibody which reacts specifically with the antigen to be determined; previously attaching, on the other hand, a second antibody which reacts specifically with the first antibody, to the reaction carrier; allowing the reaction products to migrate toward the reaction carrier by electrophoresis; passing the combined product unreacted with the first antibody, through the reaction carrier; binding the reaction product of the antigen to be determined and the first antibody reacted therewith, and the reaction product of the combined product of the same antigen as the antigen to be determined and the labeled charged substance and the first antibody reacted with this combined product, to the second antibody attached to the reaction carrier to hold them on the reaction carrier; determining the amount of the first antibody reacted with the combined product of the same antigen as the antigen to be determined and the labeled substance among the reaction products held on the carrier, by label measurement; and thereby quantitating the antigen to be determined in the sample.

A fourth method for immunoassay comprises reacting the antigen to be determined and a definite amount of the labeled same antigen as the antigen to be determined, with a definite amount of a first antibody which reacts specifically with the antigen to be determined; previously attaching, on the other hand, a second antibody which reacts specifically with the first antibody, to the reaction carrier; allowing the reaction products other than the unreacted labeled antigen to migrate toward the reaction carrier by electrophoresis; binding the reaction product of the antigen to be determined and the first antibody reacted therewith and the reaction product of the labeled antigen and the first antibody reacted therewith, to the second antibody attached to the reaction carrier to hold them on the reaction carrier; determining the amount of the first antibody reacted with the labeled antigen among the reaction products held on the reaction carrier, by label measurement; and thereby quantitating the antigen to be determined in the sample.

As a method other than the first to third methods, there can be employed a method in which the various substances which are not labeled are used in the initial stage of reaction and after electrophoresis a labeled antibody is bound to an antibody held on the reaction carrier, followed by quantitation by label measurement. In detail, this method comprises using the antigen to be determined, together with an antibody reactive specifically therewith or together with this antibody and a combined product of the same antigen as the antigen to be determined and a charged substance; reacting them in the initial stage in the same manner as in the first second or third method described above, except that the labeled antibody or the labeled charged substance is not used; allowing the reaction products to migrate toward the re action carrier by electrophoresis; combining the antibody or the charged substance held on the reaction carrier with. a labeled antibody reactive specifically therewith; determining the amount of the labeled antibody thus combined, by label measurement; and thereby quantitating the antigen to be determined in the sample.

According to the present invention, there is also provided a kit for the first method or the modification thereof mentioned above, which comprises a non-labeled or labeled antibody reactive specifically with an antigen to be determined; and a reaction carrier for electrophoresis having a same antigen as the antigen to be determined attached thereto.

BRIEF DESCRIPTION OF THE DRAWINGS

FIG. 2 shows a thyroxine ($T_4$) calibration curve according to the first method for immunoassay of the present invention.

FIG. 3 is a cortisol calibration curve according to the second method for immunoassay of the present invention.

DETAILED DESCRIPTION OF THE INVENTION

The method for immunoassay of the present invention comprises reacting an antigen to be determined which is apparently electrically neutral or has no or slight electric charge with a definite amount of an antibody to electrify the antigen or reacting an antigen to be determined which has originally an electric charge with a definite amount of an antibody to more electrify the antigen; allowing the reaction products to migrate toward a reaction carrier; holding the unreacted antibody or the reacted antibody o the reaction carrier; and determining the amount of the antigen to be determined in a sample based on the amount of the unreacted antibody or the reacted antibody on the reaction carrier.

The first to fourth methods described above are explained below with reference to the schematic view shown in FIG. 1.

Figure 1:
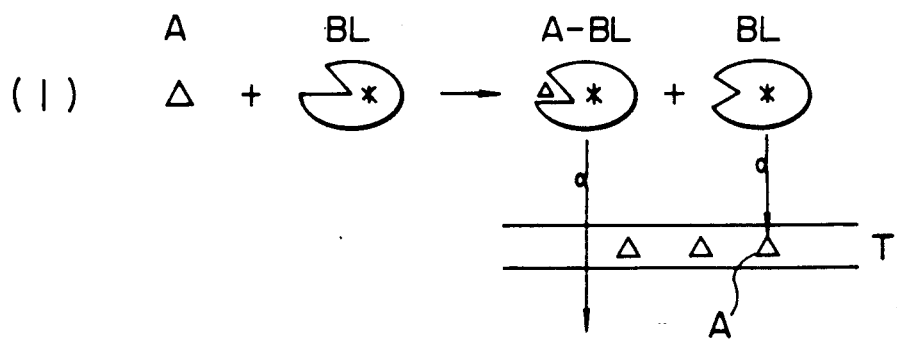
FIG. 1 is a schematic view of the immunoassay method of this invention.
Figure 1:
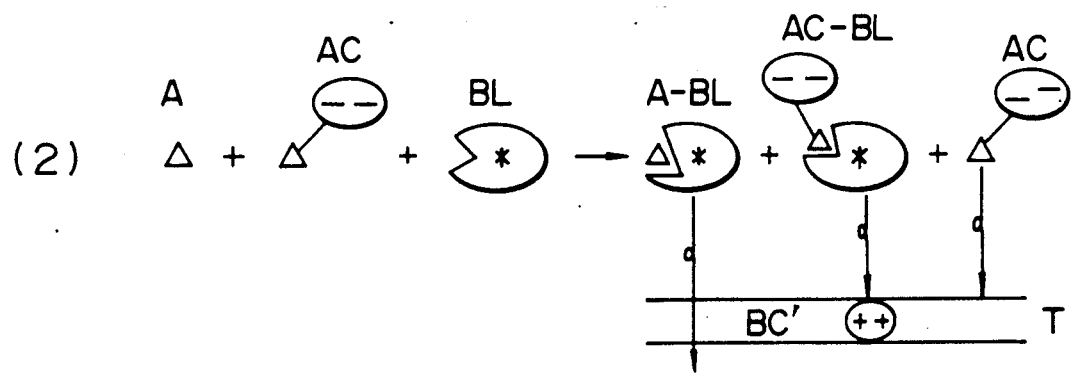
Figure 1:
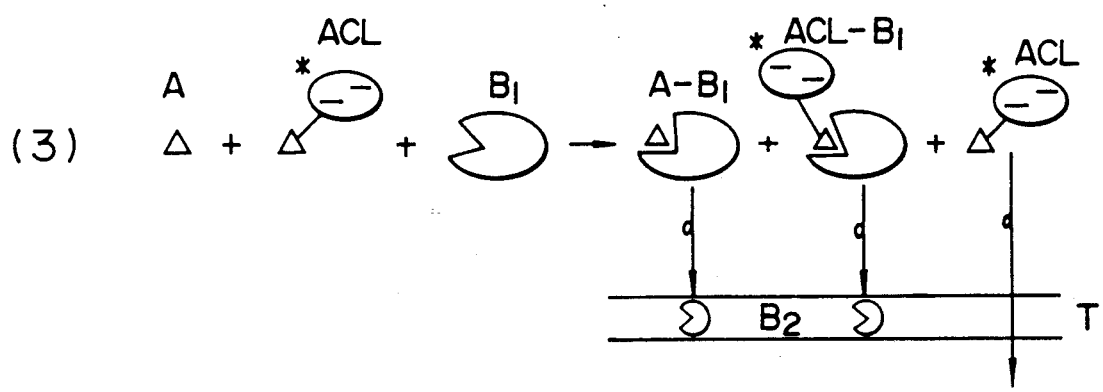
Figure 1:
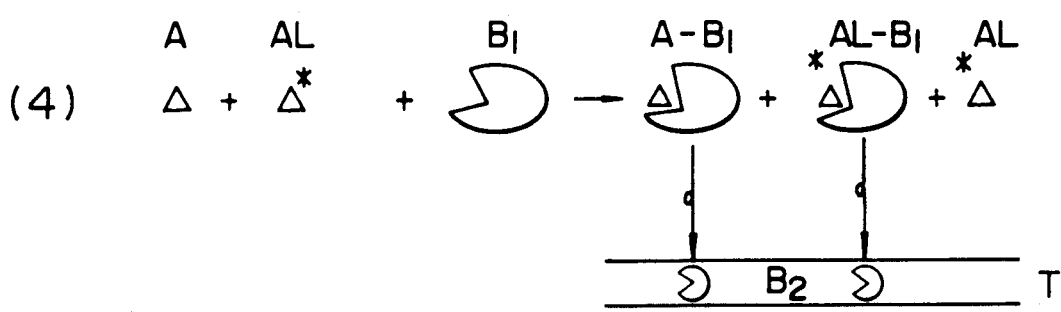

The first method is shown in FIG. 1 (1). For example, an antigen A to be determined in a sample which is apparently electrically neutral or has no or slight electric charge is reacted with a labeled antibody BL which reacts specifically with the antigen A. In the reaction solution, an antigen-antibody reaction product A-BL and the unreacted antibody BL remain. Since the antigen A is bound to the antibody BL having an electric charge, it is electrified to be enabled to migrate by electrophoresis. On electrophoresis, the antigen-antibody reaction product A-BL passes through a reaction carrier T, but the unreacted antibody BL is bound to antigen A previously attached to the reaction carrier T, so that the unreacted antibody BL is held thereon. Then, the amount of the labeled antibody BL on the reaction carrier is measured. Therefore, the antigen A can be quantitated by subtracting the amount of the unreacted antibody from the known definite amount of the labeled antibody BL before the reaction. Alternatively, when a calibration curve is previously prepared by plotting the label value against the amount of the antigen, according to the calibration curve the antigen A can be immediately quantitated from the label value measured for the antigen A in a sample.

The second method is shown in FIG. 1 (2). An antigen A to be determined in a sample and a definite amount of a combined product AC of the same antigen as the antigen to be determined and a charged substance are reacted with a definite amount of a labeled antibody BL which reacts specifically with the antigen A. In this case, the antigen A and the combined product AC competitively react with the antibody BL, and both of the resulting antigen-antibody reaction products A-BL and AC-BL have an electric charge and can migrate by electrophoresis. An antibody BC' which reacts specifically with the charged substance C is previously attached to a reaction carrier T. Although in FIG. 1 (2), the charged substance C is marked with ($--$) and the antibody BC' with ($++$), this is merely an example and respective electrification contrary to this is also possible. When the reaction products are subjected to electrophoresis, the antigen-antibody reaction product A-BL passes through the reaction carrier T, but the reaction product AC-BL and the unreacted combined product AC are held by the antibody BC' attached to the reaction carrier T. The amount of the labeled antibody in the reaction product AC-BL held on the reaction carrier is determined by label measurement. The unreacted combined product AC is not labeled and hence shows no label in the label measurement. Thus, the antigen A to be determined in the sample can be quantitated by measuring the label value of the labeled antibody in the reaction product AC-BL.

As for the charged substance used in the second method, there are exemplified a protein such as albumin including bovine serum albumin, rabbit serum albumin and human serum albumin, and globulin including $\alpha$, $\beta$ or r-globulin; and a lipid such as dicetyl phosphoric acid. The charged substance may be combined to the antigen according to a conventional method using a cross-linking agent such as glutaraldehyde. The antibody may be attached to the reaction carrier using, for example, acrolein (see U.S. Pat. No. 4,628,035).

The third method is shown in FIG. 1 (3). An antigen A to be determined in a sample and a definite amount of a combined product ACL of the same antigen as the antigen to be determined and a labeled charged substance are reacted with a definite amount of a first antibody $B_1$ which reacts specifically with the antigen A. In this case, the antigen A and the combined product ACL competitively react with the antibody $B_1$ to form antigen-antibody reaction products A-$B_1$ and ACL-$B_1$ respectively, which can immigrate by electrophoresis. A second antibody $B_2$ which reacts specifically with the first antibody $B_1$ is previously attached to a reaction carrier T. When the reaction products are subjected to electrophoresis, the antigen-antibody reaction product A-$B_1$ and the reaction product ACL-$B_1$ are held by the second antibody $B_2$ attached to the reaction carrier T, but the unreacted combined product ACL passes through the reaction carrier T. The amount of the reaction product ACL-$B_1$ held on the reaction carrier T is determined by label measurement. Thus, the antigen A to be determined can be quantitated based on the label value of the reaction product ACL-$B_1$.

As for the charged substance, the above exemplified substances may be also used in the third method. The charged substance may be labeled according to a conventional method.

The fourth method is shown in FIG. 1 (4). An antigen A to be determined in a sample and a definite amount of the labeled same antigen AL as the antigen to be determined are reacted with a definite amount of a first antibody $B_1$ which reacts specifically with the antigen A. In this case, the antigen A and the labeled antigen AL competitively react with the first antibody $B_1$ to form an antigen-antibody reaction products A-$B_1$ and AL-$B_1$ which can migrate by electrophoresis. A second antibody $B_2$ which reacts specifically with the first antibody $B_1$ is previously attached to a reaction carrier T. When the reaction products are subjected to electrophoresis, the antigen-antibody reaction product A-$B_1$ and the reaction product AL-$B_1$ are held on the reaction carrier T owing to the second antibody $B_2$. However, in the case that the labeled antigen AL is, for example, a hapten such as steroidal hormone, the unreacted labeled antigen AL is electrically neutral and hence does not migrate. The amount of the reaction product AL-$B_1$ held on the reaction carrier T is determined by label measurement. Thus, the antigen A to be determined can be quantitated based on the label value of the reaction product AL-$B_1$.

There can also be employed a method in which an antigen to be determined in a sample is quantitated in the same manner as in any of the above first to third methods, except that no labeled substance is used in the reaction of the antigen and an antibody before electrophoresis. In this case, the antigen to be determined can be quantitated by reacting the antigen with the non-labeled antibody, allowing the reaction products to arrive at a reaction carrier by electrophoretic migration, and then further reacting the reaction products or the unreacted non-labeled antibody held on the reaction carrier with a labeled antibody corresponding to the labeled substance used in each above method. For example, a modification of the first method for immunoassay is as follows. An antigen A to be determined in a sample is reacted with a non-labeled antibody BL (a first antibody) which reacts specifically with the antigen to be determined, and the reaction products are allowed to migrate in same manner as described above. The antigen-antibody reaction product A-BL resulted from the above reaction passes through a reaction carrier. However, the unreacted first antibody BL reacts with antigen previously attached to the reaction carrier to be held in the reaction carrier. Then, a labeled antibody (a second antibody) which reacts specifically with the first antibody BL is added. The antigen to be determined can be quantitated by measuring the amount of label of the reaction product of the first antibody being held on the carrier and the second antibody reacted therewith. The labeled second antibody which did not react passes through the reaction carrier.

Similarly, a modification of the second method for immunoassay is as follows. An antigen A to be determined in a sample and a combined product AC are reacted with a non-labeled antibody BL (a first antibody), and the reaction products are allowed to migrate by electrophoresis in same manner as the second method. Then, the antibody BL in the reaction product AC-BL held on the carrier owing to the antibody BC' is reacted with a labeled antibody (a second antibody) which reacts specifically with the antibody BL, and the antigen A to be determined in the sample can be quantitated by measuring the amount of label of the reacted second antibody.

Similarly, a modification of the third method for immunoassay can be conducted using a non-labeled charged substance and a labeled antibody reactive specifically therewith.

As described above, according to the methods of this invention, an antigen to be determined in a sample which is apparently electrically neutral or has no or slight electric charge is electrified by the reaction of the antigen with an antibody reactive specifically with the antigen to be enabled to migrate by electrophoresis and thereafter immunoassay is carried out by electrophoresis. Therefore, the antigen to be determined can be quantitated with high sensitivity and with high precision. As for the above antigen to be determined, there may be preferably exemplified a steroidal hormone such as thyroxine, triiodothronine, cortisol, estrogen, progesterone and teststerone; a cardiac agent such as digoxin and digitalis; an antiepileptic agent such as phenobarbital and amobarbital; and vitamins such as vitamin $D_3$.

Although in the methods described above a labeling substance held on a reaction carrier is measured, it is also possible to quantitate an antigen to be determined, by measuring a labeling substance in the reaction products which has passed through a reaction carrier.

Immunoassay of an antigen to be determined which is electrically neutral or has no or slight electric charge is described above, but needless to say, immunoassay of a charged antigen can be also carried out. In particular, immunoassay of a low concentration of charged antigen can be advantageously carried out according to the present invention, since in the case of the present invention the charged antigen is more electrified by the antigen-antibody reaction to be improved in the migration property. As for the above antigen to be determined, there may be preferably exemplified a protein antigen such as α-fetoprotein and thyroid-stimulating hormone. In particular, the protein antigen may be preferably quantitated according to the first method or the modification thereof of the present invention.

In order to conduct the first method or the modification thereof mentioned above, a kit is preferable which comprises

- a non-labeled or labeled antibody reactive specifically with an antigen to be determined; and
- a reaction carrier for electrophoresis having a same antigen as the antigen to be determined attached thereto. As for the reaction carrier, polyacrylamide gel membrane or cellulose acetate membrane may be exemplified. In addition to the above element the kit may contain a suitable buffer solution etc.

The present invention is described in more detail with reference to the examples below but is not deemed to be limited thereto.

EXAMPLE 1

According to the present invention, an antigen to be determined in a sample which is apparently electrically neutral or has no or slight electric charge is reacted with a labeled antibody which reacts specifically with the antigen to be determined. As the antigen to be determined, there can be quantitated, for example, haptens such as triiodothyronine ($T_3$), thyroxine ($T_4$), etc. As the labeling substance, fluorescent substances such as fluoresceinisothiocyanate (FITC) and tetramethylrohdamineisothiocyanate; phosphorescent substances such as luminol; enzymes such as alkaline phosphatase, peroxidase and glucosidase etc. can be used, but the labeling substance is not particularly limited thereto. The labeling substance may be attached to an antigen or an antibody according to the conventional method [Avrameas, S., Immunochemistry, 6, 43, (1969)]. A reaction carrier is provided between an anode and a cathode in an electrophetic apparatus, and, for example, in the first method of the present invention the same antigen as the antigen to be determined is previously attached to the reaction carrier. An antigen or an antibody can be attached to the reaction carrier by the use of a protein such as bovine serum albumin. As for the reaction carrier, any material used conventionally may be employed, and such material includes polyacrylamide gel and cellulose acetate membranes.

According to the first method of the present invention, the antigen to be determined in the sample is reacted with a definite amount of the labeled antibody to form a reaction product of the antigen to be determined and the labeled antibody, which product has an electric charge and hence can migrate by electrophoresis. The amount of the antigen to be determined is roughly presumed, and the labeled antibody is reacted in an amount a little larger than the presumed amount of the antigen. Then, the reaction products are allowed to arrive at the reaction carrier by electrophoresis. In this case, the reaction product of the antigen to be determined and the labeled antibody passes through the reaction carrier without reacting with the same antigen as the antigen to be determined previously attached to the reaction carrier. The unreacted labeled antibody, however, reacts with the antigen attached to the reaction carrier, to be held in the reaction carrier. After the electrophoresis, the amount of the labeled antibody held on the reaction carrier is determined by label measurement. The antigen to be determined in the sample is quantitated with high sensitivity and with high precision by measuring the difference between the amount of the labeled antibody before the reaction and that of the unreacted labeled antibody held on the reaction carrier.

Determination of $T_4$ according to the first method of the present invention A detailed explanation is given below by taking the case of quantitation of a hapten $T_4$ as antigen to be determined. As a pretreatment for attaching $T_4$ to a reaction membrane as reaction carrier, a combined product of $T_4$ and albumin was prepared. For the preparation, 200 g of bovine serum albumin (BSA) was dissolved in 500 μl of 0.1 M phosphate buffer (pH 6.8). On the other hand, 2 mg of $T_4$-free acid (mfd. by Sigma Chemical Co.) was dissolved in 4 ml of dimethylformamide, and the resulting solution was added to the BSA solution in a amount (100 μl) corresponding to 50 μg of $T_4$. The resulting solution was 10 μl of a 1.5% solution prepared by diluting 0.3 ml of 25% glutaraldehyde with phosphate buffer, thereafter the resulting mixture was allowed to stand at 25° C. for 2.5 hours. Subsequently, the mixture was applied to a Sephadex G-100 column, and a $T_4$-BSA combined product was separated by the use of phosphate buffer.

The $T_4$-BSA combined product was immobilized on a polyacrylamide gel membrane as reaction carrier in the following manner. A 0.25% aqueous acrolein solution was added to 0.5 ml of the $T_4$-BSA combined product fraction obtained in the above, and the resulting solution was allowed to stand under ice-cooling for 30 minutes. Then, this solution was sufficiently dialyzed against 0.1 M phosphate buffer, pH 7.4, containing 1/15 M NaCl (hereinafter referred to as PBS). Subsequently, to the dialyzed solution were added 1.5 ml of a 0.32 g/ml acrylamide solution, 1.5 ml of a 0.016 g/ml N,N'-methylenebisacrylamide solution, 1.25 ml of a 46 µl/ml aqueous N,N,N',N'-tetramethylethylenediamine solution and 5.75 ml of a 1.25 mg/ml ammonium persulfate solution, followed by sufficient stirring. Then, the resulting mixture was poured into a gel membrane-forming tool made of glass, and allowed to stand to be gelatinized, whereby a membrane was formed. A circular membrane having a diameter of 9 mm was cut out of the membrane formed, and used as a reaction carrier.

As an electrolyte for electrolysis, Tris-glycine buffer was used.

Measurement was carried out as follows. A commercially available fluorescence-labeled (FITC-labeled) anti-$T_4$ antibody was reacted with a $T_4$ standard sample in a known amount slightly in excess of the latter. After the reaction, the reaction solution was poured into the reaction carrier placed in an electrophoretic apparatus, and then subjected to electrophoresis at an applied voltage of 250 V for 30 minutes. Subsequently, the reaction carrier was taken out and washed with PBS, and the fluorescence intensity of the unreacted FITC-labeled anti-$T_4$ antibody held on the reaction carrier was measured. In the measurement, the exciting wavelength was 485 nm and the fluorescence measuring wavelength was 520 nm.

The fluorescence intensity was measured at various sample containing $T_4$ at various concentrations. A $T_4$ calibration curve obtained o the basis of the measurement results is shown in FIG. 2. As can be seen from FIG. 2, when the $T_4$ concentration in a sample is low, only a small amount of a reaction product of the $T_4$ in the sample and the labeled anti-$T_4$ antibody is formed in the reaction solution. However a large amount of the unreacted labeled anti-$T_4$ antibody is bond to the $T_4$-BSA combined product immobilized on the reaction carrier, so that the fluorescence intensity becomes higher which is determined by a label measurement for the bound labeled anti-$T_4$ antibody. With an increase of the $T_4$ concentration, the amount of the unreacted labeled anti-$T_4$ antibody decreases and therefore the amount of the unreacted antibody held on the reaction carrier also decreases, resulting in a low fluorescence intensity. Thus, according to the present method, the $T_4$ concentration is correlated with the fluorescence intensity with high precision, and when a calibration curve for $T_4$ concentration is previously obtained, the $T_4$ concentration can be determined by measuring the fluorescence intensity.

EXAMPLE 2

Determination of cortisol according to the second method of the present invention Cortisol was used as an antigen to be determined in a sample. A combined product of cortisol and bovine serum albumin (BSA) and a reaction carrier having anti-BSA antibody attached thereto were previously prepared in the same manner as in Example 1.

A sample containing cortisol and the cortisol-BSA combined product were reacted with a known amount of alkaline phosphatase-labeled anti-cortisol antibody. 100 µl of the reaction solution was poured into the reaction carrier placed in an electrophoretic apparatus, and then subjected to electrophoresis at 250 V for 30 minutes. Subsequently, the reaction carrier was taken out and washed with PBS. Then, the reaction carrier was immersed in a solution of substrate for alkaline phosphatase in buffer for 30 minutes, and the reaction product, held on the reaction carrier, of the cortisol-BSA combined product and the labeled anti-cortisol antibody was subjected to coloration by addition of a color producing reagent. The amount of the reaction product held on the reaction carrier was determined by measuring absorbance at a wavelength of 500 nm.

Absorbance was measured at various sample containing cortisol at various concentrations. A calibration curve obtained on the basis of the results of this measurement is shown in FIG. 3. The cortisol concentration is correlated with absorbance with high precision as in the case of the $T_4$ concentration in Example 1, and it is clear that cortisol can be quantitated with high sensitivity and with high precision.

EXAMPLE 3

Determination of $T_4$ according to the third method of the present invention $T_4$ was used as an antigen to be determined in a sample. A combined product of $T_4$ and BSA was previously prepared in the same manner as in Example 1 and labeled with FITC by a conventional method. An antibody (a second antibody) against anti-$T_4$ antibody was attached to a reaction carrier.

Figure 4:
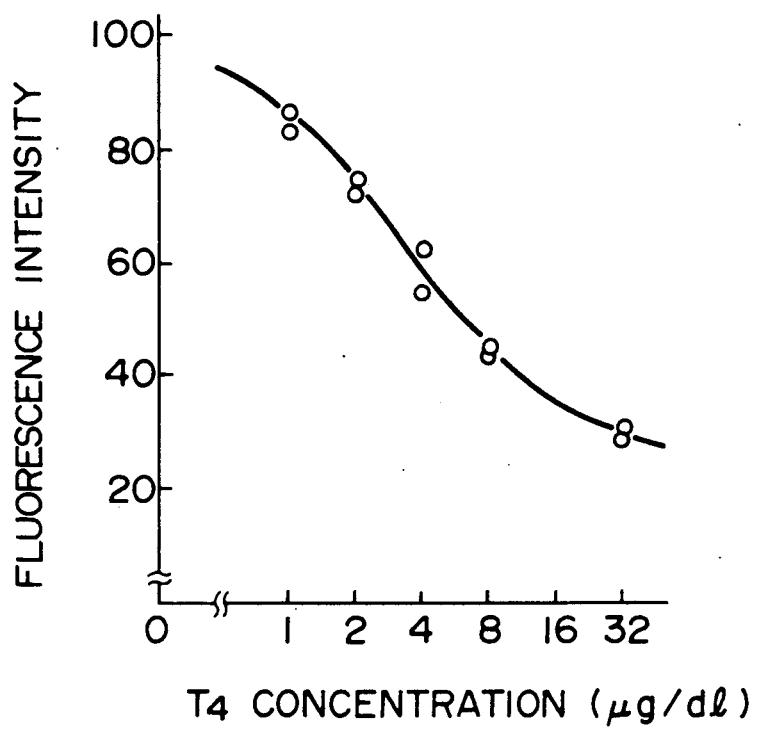
FIG. 4 is a $T_4$ calibration curve according to the third method for immunoassay of the present invention.

The sample containing $T_4$ and the $T_4$-BSA combined product labeled with FITC were reacted with anti-$T_4$ antibody 100 µl of the reaction solution was poured into the reaction carrier in an electrophoretic apparatus and then subjected to electrophoresis at an applied voltage of 250 V for 30 minutes. Subsequently, the reaction carrier was taken out and washed with PBS, followed by measurement of the fluorescence intensity of the reaction product of the $T_4$-BSA combined product labeled with FITC and anti-$T_4$ antibody, which reaction product was being held on the reaction carrier. In the measurement, the exciting wavelength was 485 nm and the fluorescence wavelength was 520 nm. A calibration curve obtain on the basis of the results of this measurement is shown in FIG. 4. The $T_4$ concentration is correlated with fluorescence intensity, and it is clear that $T_4$ can be quantitated with high sensitivity and with high precision.

EXAMPLE 4

Determination of cortisol according to the fourth method of the present invention Cortisol was used as an antigen to be determined in a sample. A cortisol-alkaline phosphatase combined product was prepared in the following manner. After 50 µl of a suspension of alkaline phosphatase in 2.6 M ammonium sulfate was centrifuged, the precipitate was dissolved in 300 µl of water. To the resulting solution were added 10 mg of 1-cyclohexyl-3-(2-morpholinyl-4-ethyl)carbodiimidomethyl-p-toluene-sulfonate and 200 µl of a solution of cortisol-21-hemisuccinate in dimethylformamide, and the reaction was carried out at room temperature for 16 hours. The emulsion thus formed was applied to Sephadex G-100 columns and eluted with 10 ml of phosphate buffer. The alkaline phosphatase activity of the eluates was measured, and two of the fractions which had the highest activity were mixed and then diluted to a volume of 10 ml with 0.05 M phosphate buffer (pH 8.0). The resulting dilution was used as alkaline phosphatase-labeled cortisol.

Figure 5:
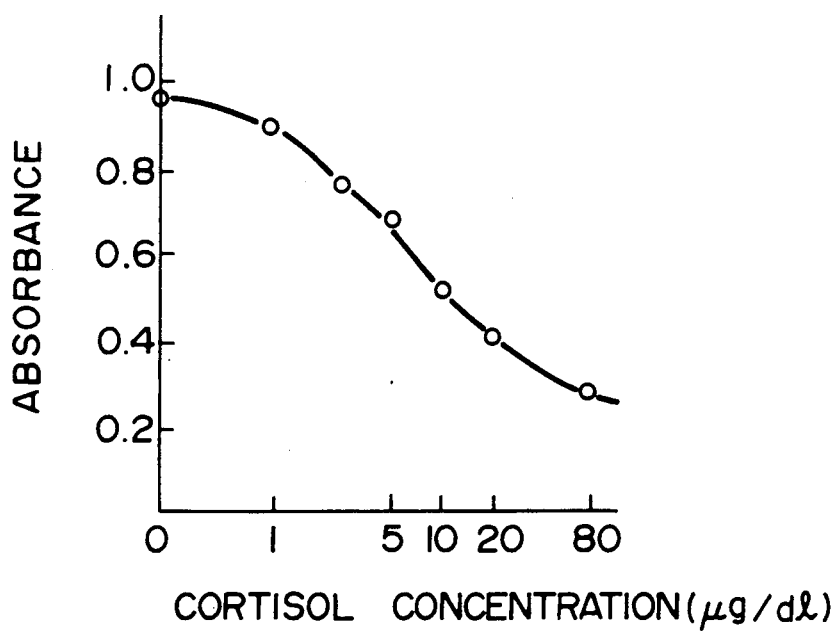
FIG. 5 is a cortisol calibration curve according to the fourth method for immunoassay of the present invention.

The sample containing cortisol and the alkaline phosphatase-labeled cortisol were reacted with anti-cortisol antibody. 100 μl of the reaction solution thus obtained was poured into a reaction carrier in an electrophoretic apparatus and then subjected to electrophoresis at 250 V for 30 minutes. As the reaction carrier, there was used one which had an antibody (a second antibody) against anti-cortisol antibody attached thereto. After the electrophoresis, the reaction carrier was taken out and washed with PBS. Then, the reaction carrier was immersed in a solution of substrate for alkaline phosphatase for 15 minutes, and the amount of the reaction product of the alkaline phosphatase-labeled cortisol and anti-cortisol antibody, which reaction product was being held on the reaction carrier, was determined by measuring absorbance at 500 nm. A calibration curve obtained on the basis of the results of this measurement is shown in FIG. 5. The cortisol concentration is correlated with absorbance, and it is clear that cortisol can be quantitated with high sensitivity and with high precision.

EXAMPLE 5

Figure 6:
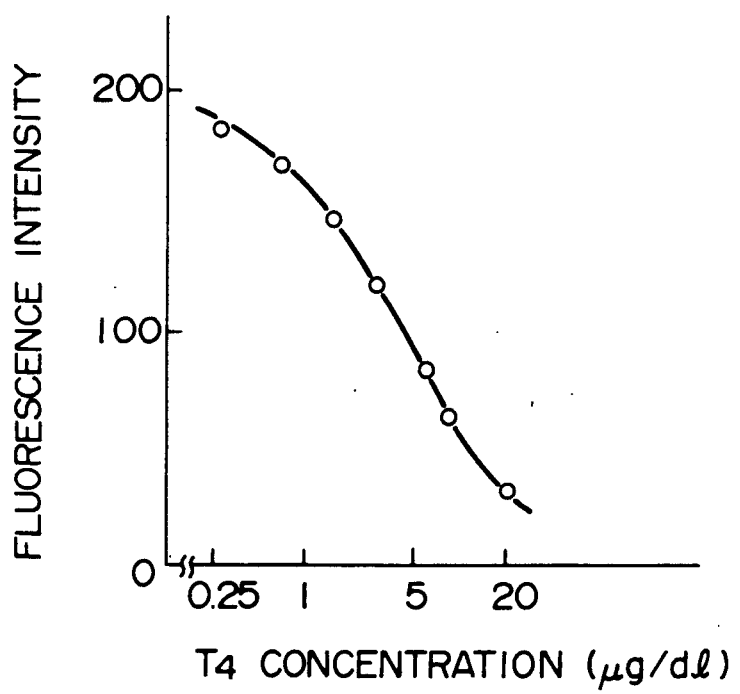
FIG. 6 is a $T_4$ calibration curve according to the modified first method for immunoassay of the present invention.

Determination of $T_4$ according to the modification of the first method of the present invention $T_4$ was used as antigen to be determined in a sample. The sample containing $T_4$ was reacted with anti-$T_4$ antibody. $T_4$ was previously attached to a reaction carrier. The reaction solution was poured into the reaction carrier in an electrophoretic apparatus and then subjected to electrophoresis at an applied voltage of 250 V for 30 minutes. Subsequently, a FITC-labeled antibody (a second antibody) to anti-$T_4$ antibody was subjected to electrophoresis at 250 V for 15 minutes. The reaction carrier was taken out and washed with PBS, followed by measurement of the amount of FITC-labeled second antibody reacted with the anti-$T_4$ antibody reacted with $T_4$ attached to the reaction carrier. In the measurement, the exciting wavelength was 485 nm and the fluorescence wavelength was 520 nm. A calibration curve obtained on the basis of the results of this measurement is shown in FIG. 6. The $T_4$ concentration is correlated with fluorescence intensity, and it is clear that $T_4$ concentration is correlated with fluorescence intensity, and $T_4$ can be quantitated with high sensitivity and with high precision.

EXAMPLE 6

Determination of a protein antigen according to the first method of the present invention α-Fetoprotein (AFP) which has an electric charge was used as an antigen to be determined in a sample. AFP was previously attached to a reaction carrier.

The sample containing AFP was reacted with FITC-labeled anti-AFP antibody. Subsequently, 200 μl of the reaction solution was poured into the reaction carrier in an electrophoretic apparatus and then subjected to electrophoresis at an applied voltage of 250 V for 30 minutes. Thereafter, the reaction carrier was taken out and washed with PBS. The amount of the FITC-labeled anti-AFP antibody held on the reaction carrier was measured at an exciting wavelength of 485 nm and a fluorescence wavelength of 520 nm.

Figure 7:
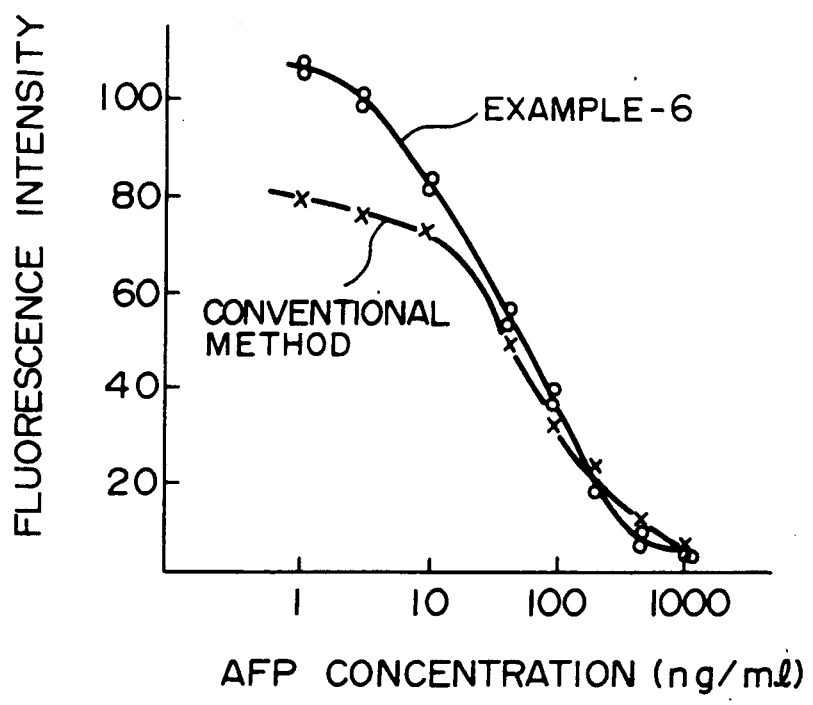
FIG. 7 is α-fetoprotein (AFP) calibration curves according to the first method for immunoassay of the present invention and a conventional method.

A calibration curve obtained on the basis of the results of this measurement is shown in FIG. 7. At the same time, a calibration curve obtained from a conventional method is also shown in FIG. 7. The conventional method is as follows. Anti-AFP antibody was previously attached to the reaction carrier. A sample containing AFP was subjected to electrophoresis, and thereafter the FITC-labeled anti-AFP antibody was subjected to electrophoresis. AFP concentration was determined by measuring the amount of the label of the FITC-labeled anti-AFP antibody held on the reaction carrier, according to a so-called sandwich method.

As is clear from FIG. 7, according to the method of the present invention, AFP can be quantitated at even low concentration with higher sensitivity and with higher precision.

According to the method for immunoassay of this invention, an antigen to be determined which is apparently electrically neutral or has no or slight electric charge is electrified by the reaction with an antibody. Therefore, such antigen can be quantitated by immunoassay using electrophoresis, and can be assayed with high sensitivity even when its concentration is very low. Moreover, it can be quantitated with high precision and high reliability. The method of the present invention is a method effective particularly in measuring a steroidal hormone.

Furthermore, according to the method of the present invention, a protein antigen which has originally an electric charge can be also quantitated with high precision and with high sensitivity.

What is claimed is:

1. A method for immunoassay for an antigen comprising:

reacting 1) a sample possibly containing an antigen to be determined, 2) a definite amount of a conjugate of the antigen and a charged substance, and 3) a definite amount of labeled antibody specific for antigen;

allowing the reaction products to electrophoretically migrate towards a carrier bearing an attached antibody specific for the charged substance, whereby when said reaction products contact said carrier 1) any reaction product of labeled antibody and antigen passes through said carrier, and 2) any reaction product of labeled antibody and conjugate binds to the carrier attached antibody specific for the charged substance;

determining the amount of labeled antibody thereby bound to the carrier;

relating the determined amount of labeled antibody to the amount of antigen in the sample.

2. A method for immunoassay for an antigen comprising:

reacting 1) a sample possibly containing an antigen to be determined, 2) a definite amount of a conjugate of the antigen and a charged substance, and 3) a definite amount of a non-labeled first antibody specific for the antigen;

allowing the reaction products to electrophoretically migrate towards a carrier bearing an attached second antibody specific for the charged substance, whereby when said reaction products contact said carrier 1) any reaction product of first antibody and antigen passes through said carrier, and 2) any reaction product of first antibody and conjugate becomes bound to the carrier attached second antibody specific for the charged substance;

reacting the first antibody thereby bound to the carrier with a labeled third antibody specific for the non-labeled first antibody;

determining the amount of labeled third antibody thereby bound to the carrier;

relating the determined amount of labeled third antibody to the amount of antigen in the sample.

3. A method of immunoassay for an antigen comprising:

reacting 1) a sample possibly containing an antigen to be determined, 2) a definite amount of a conjugate of the antigen and a labeled charged substance, and 3) a definite amount of a first antibody specific for antigen;

allowing any reaction products or unreacted conjugate to electrophoretically migrate towards a carrier bearing an attached second antibody specific for the first antibody, whereby when said reaction products or unreacted conjugate contact said carrier 1) any unreacted conjugate passes through said carrier, and 2) any reaction product of first antibody with antigen or conjugate binds to the carrier attached second antibody;

determining the amount of label in the conjugate thereby bound to the carrier;

relating the determined amount of label to the amount of antigen in the sample.

4. A method of immunoassay for an antigen comprising:

reacting 1) a sample possibly containing an antigen to be determined, 2) a definite amount of a conjugate of the antigen and a charged substance, and 3) a definite amount of a first antibody specific for the antigen;

allowing any reaction products or unreacted conjugate to electrophoretically migrate towards a carrier bearing an attached second antibody specific for the first antibody, whereby when said reaction products or unreacted conjugate contact said carrier 1) any unreacted conjugate passes through said carrier, and 2) any reaction product of first antibody with antigen or conjugate binds to the carrier attached second antibody;

reacting the conjugate thereby bound to the carrier with a labeled third antibody specific for the charged substance;

determining the amount of labeled third antibody thereby bound to the carrier;

relating the determined amount of labeled third antibody to the amount of antigen in the sample.

5. The method for immunossay according to any one of claimes 1 to 4 wherein the antigen to be determined is apparently electrically neutral or has no or slight electric chage so that the antigen cannot migrate or can slightly migrate by electrophoresis.

6. The method for immunossay according to any one of claims 1 to 4 wherein the charged substance is a protein or a lipid.

7. The method for immunossay according to claim 6 wherein the protein is bovine serum albumin, rabbit serum albumin, human serum albumin, or globulin.

8. The method for immunossay according to claim 6 wherein the lipid is dicetyl phosphoric acid.

* * * * *